United States Patent [19]

Clauder et al.

[11] 4,120,858
[45] Oct. 17, 1978

[54] 14-SUBSTITUTED VINCANES

[75] Inventors: Otto Clauder; Jozsef Kökösi; László Szporny; Egon Kárpati, all of Budapest, Hungary

[73] Assignee: Richter Gedeon Vegyeszeti Gyar Rt., Budapest, Hungary

[21] Appl. No.: 719,066

[22] Filed: Aug. 30, 1976

[30] Foreign Application Priority Data

Sep. 1, 1975 [HU] Hungary ............................ RI 577

[51] Int. Cl.² ........................................... C07D 519/04
[52] U.S. Cl. .......................... 260/293.55; 260/293.53
[58] Field of Search ....................... 260/293.55, 293.53

[56] References Cited

U.S. PATENT DOCUMENTS

| 3,455,936 | 7/1969 | Douglas et al. | 260/294.3 |
| 3,753,995 | 8/1973 | Martel et al. | 260/293.53 |
| 3,987,049 | 10/1976 | Plat et al. | 260/293.53 |
| 4,011,330 | 3/1977 | Giudicelli et al. | 260/293.53 |
| 4,021,430 | 5/1977 | Plat et al. | 260/293.53 |

OTHER PUBLICATIONS

Chemical Abstracts, 54, 16473g (1960), [Bartlett, M. F. et al., Compt. Rend., 249, 1259-1260 (1959)].
Chemical Abstracts, 70, 29146h (1969), [Blaha, K. et al., Coll. Czech. Chem. Comm., 1968, 33(11), 3833-3847].

Primary Examiner—Henry R. Jiles
Assistant Examiner—Richard A. Schwartz
Attorney, Agent, or Firm—Karl F. Ross

[57] ABSTRACT

A compound of the formula (I)

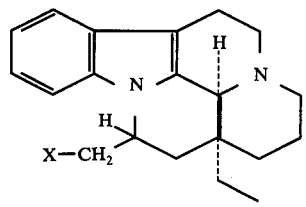

wherein X stands for a hydrogen atom, an optionally substituted aliphatic or aromatic sulfonyloxy group, a thiocyanato group, an azido group or an amino group optionally mono- or disubstituted by aliphatic, cycloaliphatic, aromatic or araliphatic hydrocarbon groups, acyl, alkyloxycarbonyl, cycloalkyloxycarbonyl, aryloxycarbonyl, aralkyloxycarbonyl, aminocarboimido groups or the substituents of the said amino group may form with the nitrogen atom thereof a five-, six- or seven-membered saturated or unsaturated heterocyclic ring optionally containing a further nitrogen, oxygen or sulfur hetero atom, and a quaternary salt or acid addition salt thereof. The compounds are useful in the treatment of arteriosclerosis and high blood pressure.

7 Claims, No Drawings

14-SUBSTITUTED VINCANES

The invention relates to 14-substituted vincane derivatives of the formula I

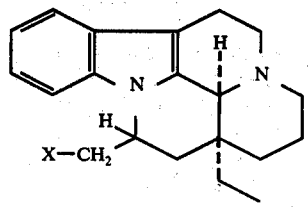

and to their epimers of the structural formulae Ia and Ib

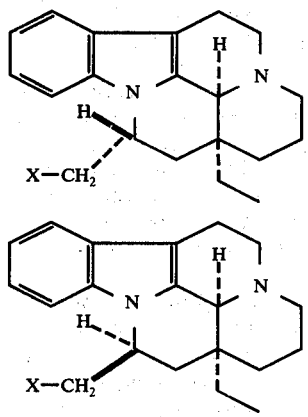

wherein X is hydrogen, a substituted or insubstituted aliphatic or aromatic sulfonyloxy group, a thiocyanato group, an azido group or an amino group which can be mono- or disubstituted by aliphatic, cycloaliphatic, aromatic or araliphatic hydrocarbon groups, acyl, alkyloxycarbonyl, cycloalkyloxycarbonyl, aryloxycarbonyl, aralkyloxycarbonyl, aminocarboimido groups or by substituted derivatives thereof, and the aliphatic hydrocarbon substituents of the said amino group may form with the nitrogen atom thereof a five-, six- or seven-membered saturated or unsaturated heterocyclic ring which can contain a further nitrogen, oxygen or sulfur hetero atom, and to the quaternary salts and acid addition salts of the said compounds, as well to a process for the preparation thereof.

The new compounds of the invention are prepared by reacting deoxyvincaminol of the formula II

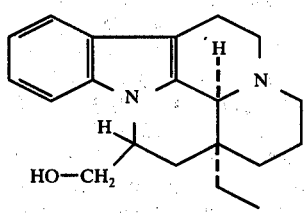

in the form of a mixture of the two possible epimers, or in the form of one of the said two epimers, i.e. deoxyvincaminol of the more specific formula IIa or epideoxyvincaminol of the more specific formula IIb

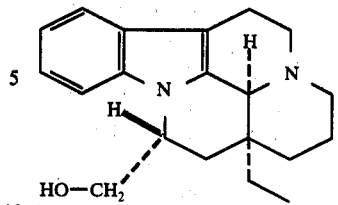

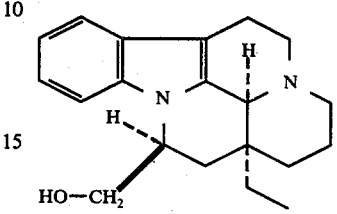

with a substituted or unsubstituted aliphatic or aromatic sulfonic acid or with a reactive derivative thereof, to yield the corresponding sulfonic acid derivative of the formula I (or Ia or Ib, respectively), wherein X is a substituted or unsubstituted aliphatic or aromatic sulfonyloxy group, and, if desired, reducing the said sulfonic acid derivative of the formula I (or Ia or Ib, respectively) to yield the corresponding compound of the formula I (or Ia or Ib, respectively), wherein X is hydrogen, or, if desired, subjecting the said sulfonic acid derivative of the formula I (or Ia or Ib, respectively) to a nucleophilic substitution with a metal salt, preferably with a metal salt of an organic sulfonic acid or with a metal thiocyanate, or with a metal azide or with an organic base, preferably with an aliphatic primary, secondary or tertiary amine, a cycloaliphatic amine, an araliphatic amine or a cyclic amine which can contain one or more hetero atoms, which can be the same or different. The obtained compounds of the formula I (or Ia or Ib, respectively), wherein the substituent X is or contains a replaceable or convertible atom or group, can be subjected to further conversion reactions. Thus if in the obtained compound of the formula I (or Ia or Ib, respectively) X is an azido group, it can be subjected to reduction, or if in the obtained compound of the formula I (or Ia or Ib, respectively) X is an amino group, it can be subjected to acylation or to alkylation or to reaction with a carbonyl compound and subsequent reduction or to reaction with a halogen carbonic acid ester or with an S-alkyl-isothiuronium salt. If desired, the obtained compound of the formula I (or Ia, or Ib, respectively) can be epimerized and/or the emperic forms of the obtained product can be separated. The obtained compound of the formula I (or Ia or Ib, respectively) can, if desired, also be converted into a quaternary salt or acid addition salt. The compound of the formula I (or Ia or Ib, respectively), if desired, can also be liberated from the obtained salt thereof.

It is known that the alkaloid vincamine has a valuable cerebral vasodilatatory effect, and especially the vincamine derivatives substituted at the 14-carbon atom are of great interest because the physiological properties of these derivatives are similar to those of vincamine. Such compounds are, for example, apovincamine obtainable by dehydrating vincamine in an acidic medium, vincamone obtainable by Curtius decomposition [cf.: Clauder et al., Tetrahedron letters 1147 (1961); Hungarian Patent Specifications No. 151,295 and 157,688], vincanol and isovincanol (Clauder et al., Hungarian Patent Specification No. 157,687), deoxyvincamine and epideoxyvincamine [J. Mokry et al., Chem. Zwesti 17, 41-53 (1963); Lloydia 27, 428 (1964)], deoxyvincaminol and epideoxyvincaminol [V. Kovacik and I. Kompis, Coll, Czech. Chem. Commun. 34, 809–818 (1969); Oliver et al., C.R. Acad. Sci. Paris, 268, 1442 (1969)], and acetyloxy derivatives of deoxyvincaminol and epideoxyvincaminol (the preparation of which is described in the French Patent Specification No. 2,035,784).

We have found that most of the compounds of the formula I and the epimers thereof of the more specific formulae Ia or Ib, respectively, have important physiological effects.

In the formulae I, Ia and Ib the substituent X may have preferably the following meanings:

As aliphatic sulfonyloxy X is preferably straight or branched chain lower alkanesulfonyloxy, e.g. methanesulfonyloxy, ethanesulfonyloxy and propanesulfonyloxy.

As aromatic sulfonyloxy X is preferably a mono- or polycyclic arylsulfonyloxy group which can contain on the aromatic nucleus one or more substituents, preferably alkyl groups, as for example benzenesulfonyloxy, p-toluenesulfonyloxy and naphthalenesulfonyloxy.

If X is an amino group mono- or disubstituted by aliphatic hydrocarbon groups, these substituents may be saturated or unsaturated straight or branched chain hydrocarbon groups, preferably alkyl groups having 1 to 6 carbon atoms or alkenyl or alkynyl groups having 2 to 6 carbon atoms.

The alkyl groups can be methyl, ethyl, n-propyl, isopropyl, n-butyl, isobutyl, tert.butyl, amyl, isoamyl, and hexyl; preferred are the methyl and ethyl groups.

The alkenyl groups may be e.g. allyl, propenyl and butenyl preferred is the allyl group.

The cycloaliphatic hydrocarbon groups may be cycloalkyl or cycloalkenyl groups having 3 to 20 carbon atoms, e.g. cyclopentyl, cyclohexyl, cycloheptyl etc. groups.

The araliphatic hydrocarbon groups have preferably 7 to 20 carbon atoms and contain mono or polycyclic aromatic moieties; such groups are e.g. the benzyl, phenylethyl, phenylpropyl, phenylbutyl, naphthylmethyl, naphthylethyl, naphthylpropyl and naphthylbutyl groups.

The acyl groups may be derived from aliphatic or aromatic carboxylic acids or from aliphatic or aromatic sulfonic acids.

The acyl groups of aliphatic carboxylic acids may be those of saturated monobasic carboxylic acids, such as formic, acetic, and propionic acids, of unsaturated monobasic carboxylic acids, such as acrylic, crotonic, vinylacetic and methyacrylic. acids; the preferred acyl is the acyl group of acetic acid. In the hydrocarbon moiety having preferably 1 to 6 carbon atoms, the said carboxylic acid may contain optionally one or more substituents. Such substituents may be halogen atoms, as fluorine, chlorine, bromine or iodine atoms attached to the same or to different carbon atoms, oxo, amino or aryl, e.g. phenyl, diphenyl, naphthyl.

The acyl groups of aromatic carboxylic acids may be those of benzoic acid, of diphenyl carboxylic acids or of naphthoic acids, optionally containing in the aromatic nucleus one or more substituents, such as alkyl, alkenyl, alkoxy, nitro, amino, hydroxy, trifluoromethyl, cyano, sulfo, thio, oxo and halogen atoms.

The acyl groups of aliphatic sulfonic acids may be those of lower alkanesulfonic acids, as of methane, sulfonic acid, ethanesulfonic acid and propanesulfonic acid.

The acyl groups of aromatic sulfonic acids may be preferably the acyl groups of the sulfonic acid derivatives of mono- or polycyclic aromatic hydrocarbons which can be mono- or polysubstituted preferably by alkyl groups in the aromatic nucleus, such as the acyl groups of benzenesulfonic acid, p-toluenesulfonic acid and naphthalenesulfonic acids.

The alkyloxycarbonyl, cycloalkyloxycarbonyl, aryloxycarbonyl and aralkyloxycarbonyl groups mentioned as possible substituents of an amino group X may be the oxycarbonyl derivatives of the hydrocarbon groups mentioned above.

If X is an amino group substituted by aliphatic hydrocarbon groups forming a heterocyclic ring with the nitrogen atom to which they are attached, this heterocyclic ring may be one of the following groups: pyrrolidino, piperidino, perhydroazepino, pyrazolidino, imidazolidino, piperazino, hexahydropyrimidino, hexhydropyridazino, hexahydrodiazepino, oxazolidino, thiazolidino, morpholino and hexahydro-oxazepino. These heterocyclic groups may be optionally substituted by halogen atoms, hydroxy, alkyl, alkoxy, amino, mercapto, trifluoromethyl, phenyl or substituted phenyl groups. Such substituted heterocyclic groups are e.g. the 3,5-dimethyl-morpholino, 4-methylpiperidino, and 4-($\beta$-hydroxyethyl)-piperazino, 4-(p-chlorophenyl)-piperazino.

Among the compounds of the formula I (or Ia or Ib, respectively) of the present invention preferred are those wherein X represents hydrogen, an unsubstituted or alkyl-substituted benzenesulfonyloxy group, a thiocyanato, azido, amino, acylamino, alkylamino, dialkylamino, alkenylamino, cycloalkylamino, aralkylamino, alkyloxycarbonylaminno or guanidino group, a five or six-membered saturated heterocyclic group containing one nitrogen atom, a six-membered saturated heterocyclic group containing two nitrogen atoms or a six-membered saturated heterocyclic group containing one nitrogen and one oxygen atom, as well as the quaternary salts and acid addition salts thereof.

Especially preferred are those compounds of the formula I (or Ia or Ib, respectively) and the salts thereof, wherein X represents hydrogen or a p-toluenesulfonyloxy, azido, thiocyanato, amino, dimethylamino, diethylamino, pyrrolidino, piperidino, morpholino, piperazino, butylamino, allylamino, cyclohexylamino, benzylamino, acetylamino, ethoxycarbonylamino or guanidino group.

In performing the preparation process of the invention, the starting compound deoxyvincaminol of the formula II, in the forms of a mixture of epimers or of one of the pure expimers, deoxyvincaminol of the formula IIa or epideoxyvincaminol of the formula IIb, is reacted with a reactive derivative of an unsubstituted or substituted aliphatic or aromatic sulfonic acid, preferably with a halide thereof. Most preferred are the acid chlorides for this purpose. Among the sulfonic acid halides, the aromatic sulfonic acid halides are preferred; these may be unsubstituted or substituted by an alkyl group. The reaction is performed preferably in the presence of an acid binding agent. An inorganic base, as an alkaline earth metal oxide, e.g. magnesium oxide, an alkali metal carbonate, e.g. potassium carbonate, or an organic tertiary base, such as pyridine or triethyl amine may be used as acid binding agent. The amount of the acid binding agent may be varied between wide limits, but preferably an amount thereof is used which is sufficient to bind the acid formed during the reaction.

In the case of using pyridine as acid binding agent, it may act simultaneously as a solvent medium for the reaction. Otherwise, the reaction can be performed in any inert organic solvent medium. The reaction is to be performed with exclusion of moisture, by using anhydrous materials. The reaction temperature may be varied according to the nature of the reacting materials; preferably the reaction may be carried out at lower temperatures.

The reduction of the obtained sulfonyloxy compounds of the formula I (or Ia or Ib, respectively), wherein X is an optionally substituted aliphatic or aromatic sulfonyloxy group, may be performed with any reducing agent capable of replacing the aliphatic or aromatic sulfonyloxy group by hydrogen. Preferred are chemical reducing agents, such as complex metal hydrides, e.g. lithium aluminum hydride. An aliphatic or cyclic ether, e.g. diethyl ether, especially anhydrous diethyl ether or tetrahydrofuran may be used preferably as solvent or suspending medium for the reduction. The reaction temperature is not of critical importance; preferably the reduction may be carried out at a temperature between the room temperature and the boiling point of the solvent used as reaction medium. The reaction time depends on the nature of the reacting materials and of the temperature; it may be between 2 and 10 hours.

The product obtained by the reduction of the compounds of formula I (or Ia or Ib, respectively), wherein X is an unsubstituted or substituted aliphatic or aromatic sulfonyloxy group, is the corresponding compound, wherein X is hydrogen, i.e. 14-methyl vincane or the epimers thereof.

The sulfonyloxy compounds of the formula I (or Ia, or Ib, respectively), wherein X is an optionally substituted aliphatic or aromatic sulfonyloxy group, obtained as described above, can be then converted, if desired, by nucleophilic substitution carried out with metal salts, to yield compounds of formula I (or Ia, or Ib, respectively) containing in the place of X the corresponding substituents other than the said sulfonyloxy groups.

As metal salts, preferably the alkali metal salts, e.g. the sodium or potassium salts of organic sulfonic acids may be used for this purpose. The reaction is carried out preferably at elevated temperature.

A specific case of the nucleophilic substitution reactions with metal salts is also the reaction with a metal isothiocyanate, preferably with an alkali metal isothiocyanate. Preferably potassium thiocyanate is used for ths purpose. The reaction can be performed in a dipolar aprotic organic solvent, preferably in dimethyl formamide. The thiocyanate is used preferably in a slight excess. The reaction is to be performed at an elevated temperature, e.g. between 70° and 130° C, and is completed in 2 to 10 hours.

The product obtained by this reaction are compounds of the formula I (or Ia, or Ib, respectively), wherein X is a thiocyanate group, i.e. 14-thiocyanatomethyl vincane or the epimers thereof.

Nucleophilic substitution reaction can be performed also with metal azides, preferably with alkali metal azide, e.g. with sodium azide. The azide is used preferably in excess in this reaction. A dipolar aprotic organic solvent, e.g. dimethyl formamide is used as solvent medium. According to a preferred method of performance, the sulfonyloxy compound is dissolved in the said organic solvent and an aqueous solution of the azide is added thereto. The reaction is carried out preferably at elevated temperature, e.g. between 70° and 130° C, and is completed in a period between 10 minutes and one hour.

The products obtained by this reaction are compounds of the formula I (or Ia or Ib, respectively), wherein X is an azido group, i.e. 14-azidomethyl vincane or the epimers thereof.

Nucleophilic substitution reaction can be performed also ammonia or with organic bases, e.g. with aliphatic primary, secondary or tertiary amines, cycloaliphatic, araliphatic or aromatic amines or with cyclic amines containing one or more equal or different hetero atoms.

The aliphatic amines may contain saturated or unsaturated, straight or branched chain hydrocarbon groups having 1 to 8 carbom atoms. The following aliphatic primary amines may be used as nucleophilic reagents: methylamine, ethylamine, n-propylamine, isopropylamine, n-butylamine, isobutylamine, sec.-butylamine, tert.-butylamine, n-pentylamine, isopentylamines, n-hexylamine, isohexylamines, n-heptylamine, isoheptylamines, n-octylamine, isooctylamines, allylamine, propenylamine, butenylamine, pentenylamine, hexenylamine, heptenylamine and octenylamine.

E.g. the following aliphatic secundary amines may be used: dimethylamine, diethylamine, di-n-propylamine, diisobutylamine, diallylamine, dipropenylamine and dibutenylamine.

As aliphatic tertiary amines, trimethylamine or triethylamine may be used.

The cycloaliphatic amines may contain a saturated hydrocarbon group of 5 to 7 carbon atoms, attached to the nitrogen atom. Such cycloaliphatic amines are cyclopentylamine, cyclohexylamine and cycloheptylamine.

The araliphatic amines may contain a mono- or polycyclic araliphatic hydrocarbon group of 7 to 20 carbon atoms, preferably an aryl-loweralkyl group, attached to the nitrogen atom. Araliphatic amines which may be used, are benzylamine, α-phenylethyl amine, β-phenylethyl amine, phenylpropyl amine, phenylbutyl amine, naphthylmethyl amine, naphthylethyl amine, naphthylpropyl or naphthylbutyl amine.

The aromatic amines may contain a mono- or polycyclic aromatic hydrocarbon group preferably of 6 to 14 carbon atoms, wherein the amino group is attached directly to the aromatic nucleus. Such aromatic amines are aniline, diphenylamine and α-naphthylamine, β-naphthylamine.

The cyclic amines may be built up of five-, six- or seven-membered saturated or unsaturated heterocyclic rings, which may contain also a further nitrogen or other, e.g. oxygen or sulfur hetero atom in addition to the amino nitrogen atom, and may be substituted by halogen atoms or hydroxy, alkyl, alkoxy, amino, trifluoromethyl, phenyl or substituted phenyl groups. Thus the following cyclic amines may be used as nucleophilic reagents: pyrrolidine, piperidine, pyrazolidine, imidazolidine, piperazine, hexahydropyrimidine, hexahydropyridazine, oxazolidine, thiazolidine, morpholine, thiomorpholine, 3,5-dimethylmorpholine, 4-methylpiperidine, 4-(β-hydroxyethyl)-piperazine and 4-(β-chlorophenyl)-piperazine.

The nucleophilic substitution reaction with organic bases is carried out preferably in an excess of the organic base; 2 to 10 moles of the organic base may be used for one mole of the compound of the formula I (or Ia, or Ib, respectively), wherein X is an optionally substituted aliphatic or aromatic sulfonyloxy group. If the organic base is used in a sufficiently great excess, it may act also as a solvent medium for the reaction. Otherwise, however, also other organic solvents, such as dimethylformamide, may be used as the reaction medium. The reaction temperature may be between the room temperature and the boiling point of the solvent or of the organic base used as reaction medium; the preferred temperature range is 25° and 200° C. The reaction time depends on the reacting materials, solvents and reaction temperature; it may be in general between 30 minutes and two weeks.

By nucleophilic substitution reaction with organic bases, compounds of the formula I (or Ia, or Ib, respectively), are prepared, wherein X is an amino group, mono- or disubstituted by aliphatic, cycloaliphatic, aromatic or araliphatic hydrocarbon group or by substituted derivatives thereof; the aliphatic substituents of the amino group X may form together with the nitrogen atom to which they are attached also a five-, six- or seven-membered saturated or unsaturated heterocyclic ring, which may contain also a further nitrogen or an oxygen or sulphur hetero atom.

These compounds can be converted, if desired, into acid addition salts by reacting them with an acid, e.g. with hydrochloric acid. According to a preferred method of performing this salt-forming reaction, the product of the nucleophilic substitution reaction with an organic base is dissolved immediately, without further purification steps, in an anhydrous aliphatic alcohol, e.g. in absolute ethanol and then an acid, e.g. dry gaseous hydrochloric acid is introduced into the solution. The formed acid addition salt is then precipitated by adding ether to the alcoholic solution.

The compounds of the general formula I (or Ia or Ib, respectively), obtained by the reaction steps described above, wherein the substituent X is or contains a group capable of further conversions, may be converted, if desired, by per se known reactions into compounds containing other substituents X within the scope of the definition of X given above.

The compounds of the general formula I (or Ia or Ib, respectively), wherein X is an azido group, i.e. 14-azidomethyl vincane or the epimers thereof, can be reduced to the corresponding compound of the general formula I (or Ia or Ib, respectively), wherein X is an amino group, i.e. to 14-aminomethyl vincane or to the epimers thereof, respectively. The reduction is carried out preferably with catalytically activated hydrogen. Metals such as palladium, platinum, nickel, iron, copper, cobalt, chromium, zinc, molybdenum, and tungsten, as well as the oxides and sulfides thereof may be used as the catalyst; preferred are the noble metal catalysts, as palladium and platinum, or Raney-nickel. The catalytic hydrogenation can be carried out also in the presence of catalysts precipitated on the surface of a carrier; in this way the desired reduction can be carried out with a substantially lesser amount of the expensive noble metals. Such carriers may be e.g. coal, especially charcoal, silica, alumina or the sulfates or carbonates of alkaline earth metals. In the reduction step with catalytically activated hydrogen according to the invention a palladium-charcoal catalyst may be used preferably, but also other catalysts may be used as well; the selection of the catalyst can be made in accordance with the nature of the compound to be reduced and with the reaction conditions. The catalytic hydrogenation is carried out in an inert solvent or in a mixture of such solvents. Preferred solvents are the aliphatic alcohols, as methanol, ethanol etc. The reaction temperature, pressure and reaction time of the catalytic hydrogenation of the process of the invention may be varied within wide limits depending on the nature of the starting materials; it is, however, preferred to perform the hydrogenation at room temperature and atmospheric pressure, until no more hydrogen is taken up by the reaction mixture. The further processing of the reaction mixture is carried out in a known manner, e.g. by filtering off the catalyst and evaporating the filtrate to dryness.

The thus-obtained compounds of the formula I (or Ia or Ib, respectively), can be converted, if desired, into acid addition salts by reacting them with an acid, as described above.

The compounds of the formula I (or Ia or Ib, respectively), wherein X is an amino group, i.e. the 14-aminomethyl vicane and its epimers, or the salts thereof can be further converted, as desired, by various reactions, to yield further new derivatives thereof.

According to such a possible further conversion, the compounds of the formula I (or Ia or Ib, respectively), wherein X is an amino group, i.e. the 14-aminomethyl vincane and its epimers, can be subjected to an acylation reaction, to yield compounds of the formula I (or Ia or Ib, respectively), wherein X is an acylamino group.

The acylation can be performed with any acylating agent used commonly in organic chemical processes. Such acylating agents may aliphatic or aromatic carboxylic acids or functional derivatives thereof, as acid halides, preferably chlorides, acid anhydrides, e.g. simple or mixed anhydrides or inner anhydrides, such as ketenes, further esters, preferably those formed with lower alkanols. The aliphatic or aromatic carboxylic acids may be those enumerated above.

The obtained acylamino compounds may be reconverted, if desired, into the amino compound by hydrolysis. This hydrolysis is performed preferably in the presence of an acid catalyst, e.g. hydrochloric or sulfuric acid.

When a free aliphatic or aromatic acid is used as acylating agent, suitably a condensing agent, preferably a water binding agent, such as dicyclohexyl carbodiimide is used to accelerate the reaction or to get it completed; if, however, the reaction components of the acylation with free acid are sufficiently reactive, the acylation process take place with sufficient reaction rate also in the absence of catalysts.

When using an aliphatic or aromatic acid halide or acid anhydride as acylating agent, it is suitable to add an acid binding agent to the reaction mixture. An inorganic base, as a metal oxide, preferably an alkaline earth metal oxide, e.g. magnesium oxide, an alkalie metal hydrocarbonate, e.g. sodium bicarbonate, an alkali carbonate, e.g. potassium carbonate or a tertiary organic base, as pyriidine or a trialkyl amine, e.g. triethylamine may be used as acid binding agent. The amount of the acid binding agent can be varied within wide limits; it is, however, suitable to use at least the amount necessary to bind the acid formed in the reaction. In cases, where the reactivity of the reaction components of the acylation reaction is sufficiently high, the acylation takes place with a sufficient reaction rate even in the absence of acid binding agents.

The acylation reaction is performed mostly in the presence of a solvent medium. This may be, in certain cases, an excess of the acylating agent, e.g. of acetic acid anhydride, or of the tertiary base used as acid binding agent, e.g. of pyridine; it is, however, possible to use any other organic solvents which are inert from the point of view of the reaction, e.g. halogenated hydrocarbons, such as chloroform, tetrachloromethane, dichloroethane, 1,2-dichloromethane or trichloromethanne, aromatic hydrocarbons, such as bennzene or toluene, acetone, ether, dioxane, tetrahydrofuran, alkanecarboxylic acid esters, such as ethylacetate, dimethylformamide, dimethylsulfoxide, as the reaction medium.

The reaction temperature of the acylation may vary within wide limits, depending on the nature of the starting materials and of the solvent.

Also the reaction time of the acylation varies within wide limits and depends on the nature of the starting materials and the temperature.

Primary amines of the formula I (or Ia or Ib, respectively), wherein X is an amino group, i.e. the 14-aminomethyl vincane and its epimers can be converted into secondary or tertiary amines, e.g. by alkylation. The alkylation reaction is performed with the usual alkylating agents, e.g. with an alkyl halide of the formula Hal-R, with a dialkyl sulfate of the formula $SO_2(OR)_2$ or with an arylsulfonic acid alkyl ester of the formula $ArSO_2$—OR; in these formulae Hal stands for a chlorine, bromine or preferably iodine atom, Ar is an aromatic group, especially a phenyl or naphthyl group unsubstitited or substituted by one or more lower alkyl groups, and R is a straight or branched chain alkyl group having 1 to 6 carbon atoms, e.g. a methyl, ethyl, n-propyl, isopropyl, n-butyl, isobutyl, sec.-butyl, tert.-butyl, n-pentyl, isopentyl, n-hexyl or isohexyl group. Such alkylating agents are e.g. methyl iodide, ethyl iodide, di-loweralkyl sulfates, e.g. dimethyl sulfate, diethyl sulfate etc., p-toluenesulfonic acid alkyl esters and the like. The acylation is carried out optionally in the presence of the usual acid binding agents, e.g. those mentioned above.

Secondary or tertiary amines can be prepared also by reacting the amino compound of the formula I (or Ia or Ib, respectively), wherein X is an amino group, i.e. 14-aminomethyl vincane or its epimers, with a carbonyl compound i.e. with an aldehyde or a ketone, and subsequently subjecting the obtained Schiff bases to catalytic hydrogenation, to yield compounds of the formula I (or Ia or Ib, respectively), wherein X is an alkylamino or dialkylamino group. The catalytic hydrogenation can be performed by the aid of the hydrogenation catalysts mentioned above.

According to a preferred method of performance, the compounds of the formula I (or Ia or Ib, respectively), wherein X is a dimethylamino group, i.e. 14-dimethylaminomethyl vincane or its epimers, respectively can be prepared by treating the starting amino compound of the formula I (or Ia or Ib, respectively), wherein X is an amino group, i.e. 14-aminomethyl vicane or its epimers, or an acid addition salt thereof with aqueous formaldehyde solution and subsequently subjecting the reaction product to catalytic hydrogenation in the presence of a palladium-charcoal catalyst.

All amino compounds prepared as described above may be converted, if desired, into acid addition salts in the known manner.

A further possible way for converting the amino compounds of the formula I (or Ia or Ib, respectively), wherein X is an amino group, i.e. 14-aminomethyl vincane and its epimers, is to react the primary amino compound with a halogen-carbonic acid ester of the formula Hal-COOR', wherein Hal is a halogen atom, e.g. fluorine, bromine, iodine or preferably chlorine, and R' is an alkyl, cycloalkyl, aryl or aralkyl group. The reaction is carried out in an inert organic solvent, preferably in a halogenated hydrocarbon, e.g. in dichloromethane. Compounds of the formula I (or Ia or Ib, respectively) are prepared in this way, wherein X is an alkyloxycarbonylamino, cycloalkyloxycarbonylamino, aryloxycarbonylamino or aralkyloxycarbonylamino group.

According to a further possible way for converting the amino compounds of the formula I (or Ia or Ib, respectively), wherein X is an amino group, i.e. 1,4-aminomethyl vincane and its epimers, into other derivatives, the said amino compounds can be reacted with an S-alkyl isothiuronium salt. The alkyl moiety of these isothiuronium salts may be straight or branched chain lower alkyl group containing preferably 1 to 6 carbon atoms, e.g. a methyl, ethyl, m-propyl, isopropyl, n-butyl, isobutyl, sec.-butyl, tert.-butyl, n-pentyl, isopentyl, n-hexyl or isohexyl. Suitablyy an isothiuronium halide, e.g. chloride, bromide or iodide, is used as isothiuronium salt; the most preferred are the S-loweralkyl-isothiuronium iodides. The reaction is carried out preferably in an inert organic solvent, preferably in an anhydrous aliphatic alcohol, e.g. in absolute ethanol. The reaction is performed suitably at moderately elevated temperatures, e.g. between 50° C and the boiling point of the solvent. The reaction time depends on the nature of the reacting materials, and of the solvent, as well on the reaction temperature; it may be in general 2 to 8 hours. Compounds of the formula I (or Ia or Ib, respectively) are obtained in this way, wherein X is an amino group substituted by an aminocarboimido group, i.e. 14-guanidinomethyl vincane or its epimers, respectively. These compounds can be converted if desired, into acid addition salts.

The compounds of the formula I, as well as the epimers thereof corresponding to the structural formulae Ia and/or Ib, wherein X is hydrogen an unsubstituted or substituted aliphatic or aromatic sulfonyloxy group, a thiocyanato group, an azido group of an amino group which can be mono- or disubstituted by aliphatic, cycloaliphatic, aromatic or araliphatic hydrocarbon group, acyl, alkyloxycarbonyl, cycloalkyloxycarbonyl, aryloxycarbonyl, aralkyloxycarbonyl or aminocarboimido groups or by substituted derivatives thereof, and the aliphatic hydrocarbon substituents of the said amino group may also form with the nitrogen atom thereof a five-, six- or seven-membered saturated or unsaturated heterocyclic ring which can contain a further nitrogen, oxygen or sulfur hetero atoms, can be converted, if desired, into quaternary salts in known manner. The formation of quaternary salts can be performed by reacting the compounds of the general formula I (or Ia or Ib, respectively), wherein X has the meaning given above, with a lower alkyl halide, e.g. with methyl iodide. The reaction is performed preferably in an inert solvent, e.g. in acetone.

The compounds of the formula I, as well as their epimers of the structural formulae Ia and/or Ib, wherein X has the same meaning as given above, can be converted also into pharmaceutically acceptable acid addition salts by reacting them with non-toxic inorganic or organic acids.

Such non-toxic inorganic acids may be hydrogen halides, such as hydrogen chloride, hydrogen bromide or hydrogen iodide, sulfuric or phosphoric acids, phosphorus acid or nitric acid. ;p As examples of suitable organic acids, the following ones may be mentioned: saturated aliphatic monocarboxylic acids, such as formic acid, acetic acid, propionic acid, caproic acid, enanthic acid, caprylic acid, pelargonic acid, caprinic acid, undecylic acid, and lauric acid, unsaturated aliphatic monocarboxylic acids, such as acrylic acid, crotonic acid, isocrotonic acid, vinylacetic acid, methacrylic acid, α-methylisocrotonic acid, oleic acid and elaidic acid; saturated aliphatic dicarboxylic acids, such as malonic acid, succinic acid, glutaric acid, α-methyl-glutaric acid, β-ethyl-glutaric acid, adipic acid, pimelic acid, suberic acid, azelaic acid and sebacic acid; unsaturated aliphatic dicarbonic acids, as maleic acid, fumaric acid, citraconic acid, mesaconic acid, itaconic acid, and acetylene dicarboxylic acid; saturated aliphatic polycarboxylic acids, such as tricarballylic acid, camphoronic acid; alkanecarboxylic acids substituted by a phenyl group, such as phenylacetic acid, phenylpropionic acid, and phenylbutyric acid; aliphatic hydroxy-mono-carboxylic acids, such as glycolic acid, lactic acid and hydracrylic acid; aliphatic hydroxy-dicarboxylic acids, such as malic acid or tartaric acid; aliphatic hydroxy-tricarboxylic acids, such as citric acid; unsubstituted or mono- or polysubstituted aromatic mono- or dicarboxylic acids, such as benzoic acid, cinnamic acid, phthalic acid, terephthalic acid, chlorobenzoic acids, methylbenzoic acids, methoxybenzoic acids, nitrobenzoic acids, anthranilic acid, p-aminobenzoic acid, salicylic acid, p-aminosalicylic acid; unsubstituted or substituted aliphatic sulfonic acids, such as methanesulfonic acid, ethanesulfonic acid, propanesulfonic acid, hydroxyethanesulfonic acid and ethylenesulfonic acid; unsubstituted or substituted aromatic sulfonic acids, such as benzene-sulfonic acids, e.g. chlorobenzenesulfonic acids, xylene-sulfonic acid, sulfanilic acid, naphthalene-1-sulfonic acid, and naphthalene-2-sulfonic acid; aminocarboxylic acids, such as methionine, tryptophane, lysine, arginine, asparaganic acid, glutamanic acid, and N-acetyl-asparaginic acid, N-acetyl-glutaminic acid; and heterocyclic acids, such as ascorbic acid.

The salt-forming reaction is carried out preferably in an inert solvent medium, suitably in an aliphatic alcohol, as methanol, ethanol, isopropanol etc. The obtained acid addition salt is then preferably precipitated from the alcoholic solution, e.g. by addition of ether.

The free compounds of the general formula I (or Ia or Ib, respectively) can be liberated, if desired, in known manner from the quaternary salts and acid addition salts prepared as described above.

In the process of the invention the product is obtained mostly in crystalline form. In cases, where the product falls out as an oil or powder, this can becrystallized from any suitably solvent used commonly in organic chemistry; oily products may be brought into crystalline form also by converting it into a salt.

The products obtained in any step of the process of the invention may be, if desired, further purified, e.g. by recrystallization before the further conversion steps.

The products of the general formula I, wherein X has the meaning as given above, may be epimerized, if desired, in known manner to yield the corresponding epimers of the formulas Ia and Ib, wherein the meaning of X is the same as above. The epimerization can be carried out in any step of the process of the invention, and then the further reaction steps can be performed with the obtained epimeric form of the compound; in this way also the end product is obtained in the form of the corresponding formula Ia or Ib, respectively.

By the process of the invention the compounds of the formula I (or Ia or Ib, respectively) and their salts can be obtained in high yields; the results of the elementary analysis of the obtained products show good agreement with the calculated values.

The new 14-substituted vincane derivatives of the invention have valuable vasoactive properties. They have the important property that they antagonize the effect of natural substances of the organism, as of norepinephrine, serotonine, histamine etc. This property can be demonstrated on experimental animals, such as on rats and dogs; in contrast to other known vasoactive compounds. However, the compounds of the invention show a prolonged duration of effect and low toxicity. The compounds of the invention also have a hyposensitive effect on dogs, but simultaneously also the amount of blood flowing through the essential organs and is increased. The antagonizing effect has been shown by the classical measuring methods on blood-vessel preparations and on rats with a destroyed spinal cord, respectively. The compounds of the invention have also spasmolytic activity, which has been demonstrated by classical techniques on isolated intestine preparations. All compounds of the invention have shown nearly equal vasoactive and spasmolytic activities.

The compounds of the invention can be used in the treatment of various diseases connected with arteriosclerosis, as well as in the supplementary treatment of high blood pressure. For these purposes the compounds can be administered in the form of free bases or of salts thereof, in the oral, parenteral or rectal way; the daily doses may be between 10 mg and 100 mg. The actual dosage is to be determined in all cases on the basis of the need of the patient, of the experiences of the physician and of the requirements of the actual case. It is to be noted that the doses mentioned above can by no means be considered as limitations of the use of the invention.

Besides their therapeutical use, the compounds of the invention can be used also as intermediate products for the preparation of other valuable, pharmacologically active products.

The pharmaceutical compositions containing the new compounds of the invention as active principles, can be prepared in per se known manner by mixing the new compounds or pharmaceutically acceptable quaternary salts or acid addition salts thereof with the usual nontoxic, inert solid or liquid carriers and/or pharmaceutical adjuvant materials, to form compositions suitable for parenteral, e.g. subcutaneous, intramuscular, intravenous and intraperitoneal, or enteral, e.g. oral, perlingual, sublingual, and rectal etc. administration. Various substances, which do not react with the new compounds, may be used as carriers, e.g. water, gelatine, lactose, starch, pectine, stearylalcohol, magnesium stearate, stearic acid, talcum, benzyl alcohols, vegetable oils, such as arachis oil and olive oil, polyalkylene glycols and vaseline. The compositions may be prepared in the usual pharmaceutical forms, e.g. as solid compositions (tablets, lozenges, dragees, capsules, e.g. hard gelatin capsules, suppositories etc.) or liquid compositions (oily or aqueous solutions, suspensions, emulsions, elixirs, syrups, soft gelatine capsules, injectable oily or aqueous solutions or suspensions etc.), or also in other forms (ointments, gelees, cremes, powders, aerosols etc.) The amount of the solid carriers in the dosage units may vary within wide limits, preferably from about 25 mg. to 1 g. The compositions may contain also the usual pharmaceutical adjuvant materials, e.g. preservatives, stabilizers, wetting agents, emulsifiers, solubilizers, substances promoting the disintegration of the tablets, salts for adjusting the osmotic pressure, buffers, flavoring or aromatizing agents. The compositions may contain, if desired, also other therapeutically valuable substances. The preparation of such pharmaceutical compositons may be performed by the usual methods, comprising the sieving, mixing, granulating and pressing the components to form solid compositions or dissolving or dispersing the active principle in liquid media to form fluid compositions. The compositions may be subjected to further pharmaceutical operations, e.g. to sterilization etc.

The process of the invention is illustrated in further details by the following examples; it is to be remarked, however, that the invention is by no means limited to the contents of these examples.

EXAMPLE 1

Preparation of apovincamine (starting material)

40 g. of vincamine are dissolved in 400 ml. of 98% formic acid and the solution is heated for 1.5 hours at 110° C. The reaction mixture is concentrated in vacuo. 200 ml. of saturated sodium carbonate solution is added to the residue and the mixture is alkalized until pH=9 with concentrated aqueous ammonium hydroxide solution. The white precipitation is filtered off, washed with distilled water and dried over phosphorus pentoxide and concentrated sulfuric acid. The obtained product is crystallized from absolute alcohol.

30.20 g. of the title compound are obtained.

Yield: 80%.

Melting point: 160°-162° C.

An additional 6.8 g. (17%) of the product can be isolated from the mother liquor.

Total yield: 37 g. (97%).

EXAMPLE 2

Preparation of epimeric Desoxyvincamine (starting material)

33.6 g. (0.1 mole) of apovincamine are dissolved in 250 ml. of glacial acetic acid and the solution is hydrogenated until the consumption of hydrogen of equivalent amount at atmospheric pressure, at room temperature for about 3 hours in the presence of 5 g. of palladium on charcoal catalyst. The catalyst is removed by filtration and the filtrate is evaporated in vacuo. 250 ml. of water are added to the residue and the mixture is alkalized under vigorous stirring with concentrated aqueous ammonium hydroxide solution. The thick solution containing the precipitate is filtered and the substance above the filter is washed with distilled water. The substance is dried over phosphorus pentoxide and concentrated sulfuric acid in vacuo. 33 g. of the named compound are obtained.

Yield: 98%.

EXAMPLE 3

Preparation of desoxyvincaminic acid (starting material)

33.8 g. (0.1 mole) of epimeric mixture of desoxyvincamine, a mixture of 11.2 g. (0.2 mole) of potassium hydroxide, 300 ml. of alcohol and 350 ml. of distilled water are stirred under refluxed at the boiling point of the mixture for 2 hours, whereafter the alcohol is evaporated and the residual aqueous solution acidified with a 2 molar solution of acetic acid until pH=3-4 under cooling and stirring, whereafter a white precipitate is obtained, which is filtered and washed with a small amount of water of pH=3. The substance is dried over phosphorus pentoxide and conc. sulfuric acid in vacuo. Thus 27.5 g. of the named compound are obtained.

Yield: 85%.

Melting point: 227°-279° C.

EXAMPLE 4

Preparation of desoxyvincamine (starting material)

300 ml. of absolute methanol are added to 32.4 g. (0.1 mole) of desoxyvincaminic acid and at 0° C an ethereal diazomethane solution is added to the mixture to maintain the yellow color. The reaction mixture is allowed to stand overnight in a refrigerator whereafter the solution is concentrated. Thus 31.2 g. of the named compound is obtained in the form of white crystals.

Yield: 82%.

Melting point: 164°-166° C.

EXAMPLE 5

Preparation of epidesoxyvincamine (starting material)

3.36 g. of epidesoxyvincamine are dissolved in acetone and the solution is mixed with distilled water until turbidity. The mixture is allowed to stand overnight in a refrigerator, while white crystals are obtained, which are filtered and washed with a small amount of alcoholic water. Thus 0.35 g. of desoxyvincamine is prepared.

Melting point: 164° C.

$[\alpha]_D = -110°$ C (c=1, in chloroform)

$R_f = 0.74$ (1) On addition of water to the mother liquor, a white crystalline substance is precipitated. The crystals are filtered and washed with distilled water. The product is recrystallized from acetone after drying. Thus 2.8 g. of epidesoxyvincamine is obtained.

Melting point: 125° C.

$[\alpha 9_D = +100°$ C (c=1, in chloroform)

Infrared spectrum: 1750 cm$^{-1}$ (—COOCH$_3$). max. 230, 284, 289.

EXAMPLE 6

Preparation of desoxyvincaminol (starting material)

33.8 g. (0.1 mole) of desoxyvincamine are suspended in 1800 ml. of dry ether and 12 g. (0.3 mole) of lithium aluminum hydride is added to the suspension in several portions. The reaction mixture is heated for 1 hour under reflux, whereafter the complex is decomposed by adding 40 ml. of distilled water dropwise at 0° C. The white precipitation thus formed is filtered off and washed with ether several times. The ether is removed by evaporation in vacuo, and as a residue 30 g. of the named compound is obtained in the form of white crystals.

Yield: 97%.

Melting point: 170° C.

EXAMPLE 7

Preparation of epidesoxyvincanol (starting material)

The product is prepared according to the method described in Example 6 except that the starting material is epidesoxyvincamine instead of desoxyvincamine. Thus the named compound melting at 205° C is obtained.

Yield: 95%.

EXAMPLE 8

Preparation of desoxyvincaminol-tosylate 15.5 g. (0.05 mole) of desoxyvincaminol are dissolved in 50 ml. of absolute pyridine and the solution is cooled to 0° C. 11.4 g. (0.06 mole) pf p-toluenesulfonic acid chloride in 50 ml. of absolute pyridine is then added dropwise to the cooled solution at 0° C. The reaction mixture is allowed to stand at 0° C for 2 hours then at room temperature for further 3 hours. The reaction mixture is then poured to a 10% sodium hydrogen carbonate solution. The obtained precipitation is extracted with 6×100 ml. of chloroform. The combined chloroform layers are washed with 100 ml. of 10% sodium hydrogen carbonate solution and with 110 ml. of distilled water, dried over sodium sulfate and evaporated in vacuo. On the addition of ether to the residue the product is partially crystallized. The pyridine is removed by evaporating twice and thus pink crystalline residue is obtained. The residue is mixed with 50 ml. of acetonitrile and the mixture is heated to boiling. The solution is allowed to stand overnight in the refrigerator and the precipitated crystals are filtered. Thus 16.3 g. of the named compound is obtained.

Yield: 70%.

Melting point: 145°–147° C.

Analysis for the formula $C_{27}H_{32}N_2O_3S$ molecular weight: 464

| calculated: | C 69.85% | H 6.90% | N 6.04% | Cl 1% |
|---|---|---|---|---|
| found: | C 69.85% | H 6.78% | N 6.56% | — |

By evaporating the mother liquor 3.5 g. (15%) of the named compound is obtained.

Total yield: 19.8 g. (85%).

EXAMPLE 9

Preparation of epidesoxyvincaminol-tosylate 3.1 g. (0.1 mole) of epidesoxyvincaminol is dissolved in 15 ml. of dry pyridine and 2.38 g. (0.0125 mole) of p-toluene sulfonic acid chloride dissolved in 15 ml. of dry pyridine is added to the solution dropwise at 0° C. The reaction mixture is allowed to stand for 24 hours at room temperature. 150 ml. of saturated sodium hydrogen carbonate solution is then added to the mixture and the obtained precipitate is extracted with 3×60 ml. of chloroform. The chloroform extract is washed with 2×25 ml. of saturated aqueous sodium hydrogen carbonate solution and with 25 ml. of water, dried over anhydrous sodium sulfate and evaporated in vacuo. The residue is evaporated to dryness with 2×25 ml. of ether to remove pyridine. 20 ml. of acetonitrile are added to the pale pink residue, whereupon white crystals are precipitated. The crystalline solution is allowed to stand in refrigerator overnight. The crystals are filtered the following day and washed with a small amount of acetonitrile. Thus 3.00 g. of the named compound is obtained.

Yield: 60%.

Melting point: 164°–166° C.

Analysis for the formula $C_{27}H_{32}N_2O_3S$ molecular weight: 464

| calculated: | C 69.85% | H 6.90% | N 6.04% |
|---|---|---|---|
| found: | C 69.70% | H 6.81% | N 6.37% |

EXAMPLE 10

Preparation of 14-(thiocyanato-methyl)-vincane 4.64 g. (0.01 mole) of desoxyvincaminol tosylate are dissolved in 50 ml. of dimethylformamide and 2 g. (0.02 mole) of potassium rhodanide dissolved in 4 ml. of water are added to the solution. The reaction mixture is heated for 6 hours at 100° C and the cooled solution is poured to 400 ml. of 10% aqueous sodium hydrogen carbonate solution and the fluffy precipitation is filtered off. The precipitation is taken up in 100 ml. of dichloromethane and washed with 2×20 ml. of 10% aqueous sodium hydrogen carbonate solution and with a small amount of water. The dichloromethane solution is dried over anhydrous sodium sulfate and evaporated in vacuo. The residue is recrystallized from the mixture of acetone and water and from methanol. Thus 2.9 g. of the named compound is obtained.

Yield: 82.5%.

Melting point: 172°–174° C.

Analysis for the formula $C_{21}H_{25}N_3S$ molecular weight: 351

| calculated: | C 71.80% | H 7.12% | N 11.96% |
|---|---|---|---|
| found: | C 71.43% | H 7.18% | N 12.25% |

EXAMPLE 11

Preparation of 14-(azido-methyl)-vincane 4.64 g. (0.01 mole) of desoxyvincaminol tosylate are dissolved in 46.4 ml. of dimethylformamide and 1.625 g. (0.025 mole) of sodium azide dissolved in 6 ml. of water is added. The reaction mixture is heated for half an hour at 100° C. After cooling, the reaction mixture is poured into 400 ml. of 10% aqueous sodium hydrogen carbonate solution and the mixture containing the precipitate is extracted with 3×100 ml. of ether. The combined ether layers are washed with a small amount of water, dried over anhydrous sodium sulfate and evaporated in vacuo. The dry residue is dried over phosphorus pentoxide and concentrated sulfuric acid in vacuo. Thus 3.2 g. of yellowish white oil of the named compound is obtained.

Yield: 96%.

EXAMPLE 12

Preparation of 14-(azidomethyl)-$N_b$-methylvincanium iodide 0.355 g. (1 mmole) of 14-(azidomethyl)-vincane is dissolved in 4 ml. of absolute acetone and 0.5 ml. of methyl iodide is added to the solution. The reaction mixture is allowed to stand at room temperature overnight. The following day ether is added dropwise to the reaction mixture, whereupon an oily precipitate is obtained. The solvent is decanted and the precipitate is treated with 2×5 ml. of absolute ether. The precipitate is then dissolved in methanol and dry ether is added dropwise to the solution until turbidity. The mixture is allowed to stand in the refrigerator. Thus 0.31 g. of the named yellowish white crystalline compound is obtained.

Yield: 65%.

Melting point: 194°–195° C (decomposition).

EXAMPLE 13

Preparation of 14-(aminomethyl)-vincane dihydrochloride 0.335 g. (1 mmole) of 14-azidomethyl vincane is dissolved in 12 ml. of absolute ethanol and the solution is hydrogenated at room temperature at atmospheric pressure with 0.4 g. of 10% palladium on charcoal catalyst for 6 hours. (The apparatus is now and then rinsed with hydrogen). The catalyst is then filtered and two thirds of the alcohol is removed by evaporation. The residue is saturated with dry hydrochloric acid gas. Absolute ether is added dropwise to the solution whereupon white crystals are precipitated. The crystals are filtered and washed with ether. Thus 0.32 g. of the named compound is obtained.

Yield: 84%.

Melting point: 280° C (the product becomes brown and decomposes). Analysis for the formula $C_{20}H_{29}N_3Cl_2$ molecular weight: 382

| | | | | |
|---|---|---|---|---|
| calculated: | C 62.83% | H 7.64% | N 10.99% | Cl 18.54% |
| found: | C 62.42% | H 7.69% | N 10.70% | Cl 18.63% |

EXAMPLE 14

Preparation of 14-(dimethylamino-methyl)-vincane dihydrochloride (a) 0.382 g. (1 mmole) of 14-(aminomethyl)-vincane dihydrochloride is dissolved in 6 ml. of water and the solution is mixed with 0.2 ml. of 30% formalin (2 mmole). The mixture is hydrogenated with 0.4 g. of 10% palladium on charcoal catalyst for about 3 hours at room temperature and at atmospheric pressure until the consumption of two equivalents of hydrogen. The catalyst is removed by filtration. The mixture is alkalized with sodium hydrogen carbonate and extracted with 3×10 ml. of ether. The ether layer is washed with a small amount of water and dried over anhydrous sodium sulfate and evaporated in vacuo. The dry residue is dissolved in 3 ml. of absolute alcohol and saturated with dry hydrochloric acid gas. Ether is added dropwise to the solution, whereupon white crystals are precipitated. The crystals are filtered and washed with ether. Thus 0.312 g. of the named compound is prepared.

Yield: 76%.

Melting point: 260° C (decomposition), (recrystallization at 220° C).

(b) 0.116 g. (0.25 mmole) of desoxyvincaminol tosylate is dissolved in 3 ml. of dimethylformamide and 2 ml. of 33% alcoholic dimethylamine solution is added to the solution. The reaction mixture is allowed to stand for a fortnight at room temperature. The alcohol is then removed from the reaction mixture by distillation. The residual dimethylformamide solution is poured into 20 ml. of 5% aqueous sodium hydrogen carbonate solution and it is further worked up according to Example a). Thus 0.082 g. of the named compound is obtained.

Yield: 80%

Melting point: 258° C.

Analysis for the formula $C_{22}H_{33}N_3Cl_2$ molecular weight: 410

| | | | | |
|---|---|---|---|---|
| calculated: | C 64.40% | H 8.12% | N 10.24% | Cl 17.24% |
| found: | C 63.90% | H 8.31% | N 10.62% | Cl 16.94%. |

EXAMPLE 15

Preparation of 14-(diethylamino-methyl)-vincane dihydrochloride 0.232 g. (0.5 mmole) of desoxyvincaminol tosylate is dissolved in 3 ml. of dimethylformamide and 1 ml. (0.7 g., 0.01 mole) of diethyl amine is added to the solution. The reaction mixture is kept for 8 hours at 50° C. whereafter the excess of the diethylamine is distilled off in vacuo. The dimethylformamide solution is poured into 20 ml. of 5% aqueous sodium hydrogen carbonate solution and the obtained precipitation is extracted with 3×15 ml. of ether. The reaction mixture is worked up according to the method described in Example 14. Thus 0.147 g. of the named compound is prepared.

Yield: 67%

Melting point: 248° C (decomposition), recrystallization at 217° C. Analysis for the formula $C_{24}H_{37}N_3Cl_2$ molecular weight: 438

| | | | | |
|---|---|---|---|---|
| calculated: | C 65.74% | H 8.51% | N 9.58% | Cl 16.17% |
| found: | C 65.08% | H 8.94% | N 9.46% | Cl 15.83%. |

EXAMPLE 16

Preparation of 14-(pyrrolidino-methyl)-vincane 0.464 g. (1 mmole) of desoxyvincaminol tosylate is heated in the mixture of 4 ml. of pyrrolidine and 2 ml. of dimethylformamide at 50° C. The excess pyrrolidine is then distilled off and the dimethylformamide solution is poured into 40 ml. of 5% aqueus sodium hydrogen carbonate solution. A white precipitate is obtained, which is filtered and washed with water. The substance is dried over phosphorus pentoxide and concentrated sulfuric acid in vacuo. Thus 0.40 g. of the named compound is obtained.

Yield: 90%

Melting point: 90°-92° C.

Analysis for the formula $C_{24}H_{33}N_3$ molecular weight: 363

| | | | |
|---|---|---|---|
| calculated: | C 79.34% | H 9.09% | N 11.57% |
| found* | C 79.10% | H 9.10% | N 11.60%. |

EXAMPLE 17

Preparation of 14-(pyrrolidinomethyl)-vincane dihydrochloride 4.64 g. (0.01 mole) of desoxyvincaminol tosylate are dissolved in 40 ml. of pyrrolidine and the solution is heated under reflux for 2 hours. The excess pyrrolidine is distilled in vacuo. The residue is dissolved in 120 ml. of dichloromethane and the solution is extracted with 2×30 ml. of water. The dichloromethane solution is dried over anhydrous sodium sulfate and evaporated in vacuo. The colorless oil obtained as residue is kept in vacuum desiccator, whereupon a crystalline mass is obtained which is dissolved in 30 ml. of absolute alcohol and the solution is saturated with dry hydrochloric acid gas. Ether is added to the solution, whereupon white crystals are precipitated, the crystals are filtered and washed with absolute ether, and dried in vacuo over phosphorus pentoxide and concentrated sulfuric acid. Thus 4.05 g. of the named compound is obtained.

Yield: 93%

Melting point: 287° C (decomposition).

Analysis for the formula $C_{24}H_{33}N_3Cl_2$ molecular weight: 436

| | | | | |
|---|---|---|---|---|
| calculated: | C 66.05% | H 8.08% | N 9.63% | Cl 16.24% |
| found: | C 65.91% | H 8.19% | N 9.47% | Cl 16.07%. |

EXAMPLE 18

Preparation of 14-(piperidinomethyl)-vincane dihydrochloride (a) 0.464 g. (0.1 mmole) of desoxyvincaminol tosylate is dissolved in 2 ml. of dimethylformamide and 0.1 ml. (1.3 mmole) of piperidine are added to the solution. The reaction mixture is kept for 1 hour at 90° C. After cooling the mixture is poured into 20 ml. of 10% aqueous sodium hydrogen carbonate solution, whereupon a white precipitate is formed, which is filtered and dried in vacuo over phosphorus pentoxide and concentrated sulfuric acid. The substance is dissolved in 4 ml. of absolute alcohol and dry hydrochloric acid gas is introduced to the solution. Ether is added to the solution whereupon white crystals are precipitated, the crystals are filtered and washed with absolute ether. Thus 0.37 g. of the named compound is obtained.

Yield: 80%.

Melting point: 245°–246° C (decomposition).

(b) 4.64 g. (0.01 mole) of desoxyvincaminol tosylate are dissolved in 30 ml. of piperidine and the solution is heated under reflux for 2 hours. The excess piperidine is then distilled in vacuo. The residue is dissolved in 120 ml. of dichloromethane and the solution is washed with 2×30 ml. of water, dried over heated sodium sulfate, the solvent is distilled in vacuo. The residue is dried in a desiccator in vacuo and a crystalline mass is obtained, which is dissolved in 30 ml. of absolute alcohol and saturated with dry hydrochloric acid gas. Ether is added to the solution whereupon white crystals are precipitated. After allowing the solution to stand overnight the crystals are separated by filtration and washed with absolute ether. Thus 4.3 g. of the named compound are obtained.

Yield: 96%.

Melting point: 256° C (decomposition beginning at 245° C)

Analysis for the formula $C_{25}H_{37}N_3Cl_2$ molecular weight: 450

| | | | | |
|---|---|---|---|---|
| calculated: | C 66.66% | H 8.28% | N 9.32% | Cl 15.74% |
| found: | C 66.14% | H 8.19% | N 9.26% | Cl 15.60%. |

EXAMPLE 19

Preparation of 14-(morpholinomethyl)-vincane 0.25 g. of desoxyvincaminol tosylate is dissolved in 2 ml. of morpholine and heated for 4 hours under reflux. The morpholine is removed by distillation in vacuo and the residue is taken up in 10 ml. of chloroform and washed with 2×10 ml. of 10% aqueous sodium hydrogen carbonate solution and 10 ml. of distilled water. The chloroform layer is dried over anhydrous sodium sulfate and evaporated in vacuo. The substance solidifies to a crystalline mass upon standing. The product is recrystallized from alcohol. Thus 0.19 g. of the named compound is obtained.

Yield: 93%.

Melting point: 133°–134° C.

Analysis for the formula $C_{24}H_{33}N_3O$ molecular weight: 379

| | | | |
|---|---|---|---|
| calculated: | C 75.95% | H 8.76% | N 11.07% |
| found: | C 76.12% | H 8.56% | N 10.98%. |

EXAMPLE 20

Preparation of 14-(morpholinomethyl)-vincane dihydrochloride 0.19 g. of 14-(morpholinomethyl)-vincane is dissolved in 3 ml. of absolute alcohol and the solution is saturated with dry hydrochloric acid gas. Absolute ether is added to the solution, whereupon white crystals are formed, which are allowed to stand overnight and filtered and washed with a mixture of alcohol and ether. Thus 0.2 g. of the named compound is obtained.

Yield: 82%.

Melting point: 236° C (decomposition).

Analysis for the formula $C_{24}H_{35}N_3OCl_2$ molecular weight: 452

| | | | | |
|---|---|---|---|---|
| calculated: | C 63.71% | H 7.80% | N 9.24% | Cl 15.67% |
| found: | C 63.58% | H 7.69% | N 8.94% | Cl 15.50% |

EXAMPLE 21

Preparation of 14-(piperazinomethyl)-vincane 0.2 g. of desoxyvincaminol tosylate and 0.16 g. of piperazine are dissolved in 2 ml. of dimethylformamide and the solution is kept for 5 hours at 100° C. After cooling the mixture is poured to 20 ml. of 5% aqueous sodium hydrogen carbonate solution, whereupon white crystals are formed, which are allowed to stand for a short time, then filtered and washed with distilled water. The substance is dried over phosphorus pentoxide and potassium hydroxide in vacuo and crystallized from methanol. Thus 0.14 g. of the named compound is obtained.

Yield: 86%.

Melting point: 230° C (decomposition).

Analysis for the formula $C_{24}H_{34}N_4$ molecular weight: 378

| | | | |
|---|---|---|---|
| calculated: | C 76.15% | H 9.05% | N 14.80% |
| found: | C 75.83% | H 8.98% | N 15.12%. |

EXAMPLE 22

Preparation of 14-(butylaminomethyl)-vincane 0.2 g. of desoxyvincaminol tosylate is dissolved in 3 ml. of freshly distilled butylamine and the solution is heated under reflux for 4 hours. The butylamine is distilled off in vacuo. The residue is dissolved in 20 ml. of chloroform and washed with 10 ml. of 10% aqueous sodium carbonate solution and 10 ml. of distilled water and dried over anhydrous sodium sulfate. The chloroform solution is distilled in vacuo and thus white oil is obtained. Thus 0.16 g. of the named compound is prepared.

Yield: 95%.

EXAMPLE 23

Preparation of 14-(butylaminomethyl)-vincane dihydrochloride 0.16 g. of 14-(butylaminomethyl)-vincane is dissolved in 3 ml. of absolute alcohol. Dry hydrochloric acid gas is introduced into the solution, whereupon a white gelatinous substance is precipitated. The substance is allowed to stand overnight in the refrigerator, filtered the following day and the product is washed with ether. The substance is dried over phosphorus pentoxide and potassium hydroxide in vacuo, thus a crystalline substance is obtained which can be easily worked up. 0.14 g. of the named compound is obtained.

Yield: 74%.

Melting point: 253° C (decomposition).

Analysis for the formula $C_{24}H_{37}N_3Cl_2$ molecular weight: 438

| calculated: | C 65.74% | H 8.51% | N 9.58% | Cl 16.17% |
|---|---|---|---|---|
| found: | C 65.62% | H 8.53% | N 9.73% | Cl 16.10%. |

EXAMPLE 24

Preparation of 14-(allylaminomethyl)-vincane 0.2 g. of desoxyvincaminol tosylate is dissolved in 3 ml. of allylamine and the solution is heated under reflux for 5 hours. The excess amine is then removed by distillation in vacuo. The residue is dissolved in 10 ml. of dichloromethane and the solution is washed with 5 ml. of 5% aqueous sodium hydrogen carbonate solution and 5 ml. of water. The dichloromethane solution is dried over anhydrous sodium sulfate, whereafter the solvent is distilled in vacuo. Thus 0.15 g. of the named compound is obtained.

Yield 97%.

EXAMPLE 25

Preparation of 14-(allylaminomethyl)-vincane dihydrochloride 0.15 g. of 14-(allylaminomethyl)-vincane is dissolved in 3 ml. of absolute alcohol and the solution is saturated with dry hydrochloric acid gas. Absolute ether is added whereupon white gel-type precipitate is formed. The precipitate is filtered and the substance above the filter is washed with absolute ether. Thus 0.12 g. of the named compound is obtained.

Melting point: 236° C (decomposition).

Analysis for the formula $C_{23}H_{33}N_3Cl_2$ molecular weight:422

| calculated: | C 65.40 | H 7.87% | N 9.94% | Cl 16.79% |
|---|---|---|---|---|
| found: | C 65.39 | H 7.84% | N 10.10% | Cl 16.60%. |

EXAMPLE 26

Preparation of 14-(cyclohexylaminomethyl)-vincane p-toluene sulfonate and 14-(cyclohexylaminomethyl)vincane dihydrochloride 0.2 g. of desoxyvincaminol tosylate is dissolved in 3 ml. of cyclohexylamine and the solution is heated for 6 hours at 100° C. After cooling white crystals are precipitated. The mixture is allowed to stand overnight, filtered and the substance above the filter is washed with methanol. Thus 0.12 g. of 14-(cyclohexylaminomethyl)-vincane p-toluenesulfonate is prepared.

Melting point: 180° C.

The mother liquor is evaporated in vacuo and the residue is dissolved in 10 ml. of dichloromethane and washed with 10 ml. of 5% aqueous sodium hydrogen carbonate and 10 ml. of distilled water. The dichloromethane solution is dried over anhydrous sodium sulfate and the dichloromethane is removed by evaporation in vacuo. The residue is dissolved in 3 ml. of absolute alcohol and dry hydrochloric acid gas is introduced into the solution. White gel-like substance is precipitated, which is filtered and washed with alcohol and with a small amount of ether. The substance is dried over phosphorus pentoxide in vacuo. Thus 0.08 g. of 14-(cyclohexylamino-methyl)-vincane dihydrochloride is obtained.

Melting point: 278°-282° C.

Analysis for the formula $C_{26}H_{39}N_3Cl_2$ molecular weight: 464

| Calculated: | C 67.22% | H 8.46% | N 9.05% | Cl 15.27% |
|---|---|---|---|---|
| found: | C 67.42% | H 8.66% | N 8.82% | Cl 15.10%. |

EXAMPLE 27

Preparation of 14-(benzylamino-methyl)-vincane dihydrochloride 0.20 g. of desoxyvincaminol tosylate is dissolved in 0.20 g. of desoxyvincaminol tosylate and the solution is heated for 3 hours at 160° C. The mixture is then poured into 20 ml. of saturated aqueous sodium hydrogen carbonate solution, whereupon a white precipitate is formed. The mixture is allowed to stand for a short time, whereafter the solution is decanted and the precipitate is washed with a small amount of water. The precipitate is dried in vacuo, dissolved in absolute alcohol and dry hydrochloric acid gas is introduced into the solution, whereafter a white precipitate is formed. The mixture is allowed to stand in the refrigerator overnight. The precipitate is filtered and washed with a small amount of absolute alcohol. Thus 0.187 g. of the named compound is obtained.

Yield: 92%.

Melting point: 210°-212° C.

Analysis for the formula $C_{27}H_{35}N_3Cl_2$ molecular weight: 472

| calculated: | C 68.64% | H 7.46% | N 8.89% | Cl: 15.01% |
|---|---|---|---|---|
| found: | C 68.34% | H 7.47% | N 9.18% | Cl 14.95%. |

EXAMPLE 28

Preparation of 14-(acetamido-methyl)-vincane (a) 0.155 g. (0.5 mmole) of 14-(amino-ethyl)-vincane is dissolved in a 5 ml. of acetic acid anhydride and the solution is heated in nitrogen atmosphere for 4 hours at 100° C. The acetic acid anhydride is then removed by distillation in vacuo. The residue is taken up in 20 ml. of dichloromethane, washed with 3×10 ml. of 10% aqueous sodium hydrogen carbonate solution and with 10 ml. of water, dried over anhydrous sodium sulfate and evaporated in vacuo. The residual yellow gum is crystallized from the mixture of alcohol and water. Thus 0.11 g. of the title compound is obtained.

Melting point: 178°-181° C.

(b) 0.155 g. (0.5 mmole) of 14-(aminoethyl)-vincane is dissolved in 4 ml. of dichloromethane and 0.05 g. (0.5 mmole) of ethyl ester of chlorocarbonic acid is added to the solution. The solution is heated under reflux for 4 hours. The solution is then diluted with 15 ml. of dichloromethane and washed with 2×10 ml. of 10% sodium hydrogen carbonate solution and with a small amount of water. The mixture is dried over anhydrous sodium sulfate. The dried solution is evaporated in vacuo. The residue is treated with the mixture of ether and petroleumether and thus a white amorphous precipitate is obtained. Thus 0.10 g. of the named compound is obtained.

Analysis for the formula $C_{22}H_{20}N_3O_2$ moleculr weight: 351

| | |
|---|---|
| calculated: | N: 11.96% |
| found: | N: 12.03%. |

EXAMPLE 30

Preparation of 14-(guanidino-methyl)-vincane dihydrochloride 0.155 g. (0.5 mmole) of 14-(aminomethyl)-vincane is dissolved in 5 ml. of absolute alcohol and 0.1 g. of S-methylisothiuronium iodide is added to the solution. The solution is heated in nitrogen stream for 4 hours under reflux. The reaction mixture is then evaporated in vacuo. The residual yellowish white foam is mixed with 10 ml. of 5% aqueous sodium hydrogen carbonate solution and the solution is extracted with 2×10 ml. of chloroform. The chloroform layer is washed with a small amount of water, dried with anhydrous sodium sulfate and evaporated in vacuo. The residue is taken up in absolute alcohol and saturated with dry hydrochloric acid gas and ether is then added dropwise. The dark precipitate formed at the beginning is filtered off. Additional ether is then added to the filtrate, whereupon white crystalline substance is precipitated. Thus 0.12 g. of the named compound is obtained.

Yield: 56%.

Melting point: 235° C (decomposition).

Analysis for the formula $C_{21}H_{31}N_5Cl_2$ molecular weight: 424

| | | |
|---|---|---|
| calculated: | N: 16.50% | Cl: 16.71% |
| found: | N: 16.67% | Cl: 16.38%. |

EXAMPLE 31

Preparation of 14-methyl-vincane 0.464 g. (1 mmole) of desoxyvincaminol tosylate is suspended in 40 ml. of absolute ether and 0.3 g. of lithium aluminium hydride is added uner vigorous stirring. The reaction mixture is stirred for 2 hours at room temperature and heated for 4 hours under reflux. The formed complex is decomposed with water. The white precipitate is filtered off and washed with 30 ml. of ether. The ether is removed from the filtrate by evaporation in vacuo. The residual oily product crystallizes on standing. Thus 0.29 g. of the named compound is obtained.

Yield: 99%.

Melting point: 102°–104° C.

Analysis for the formula $C_{20}H_{26}N_2$ moleculr weight: 294

| | | | |
|---|---|---|---|
| calculated: | C: 81.7% | H: 8.92% | N: 9.50% |
| found: | C: 81.63% | H: 8.96% | N 9.46%. |

What we claim is:

1. A compound of the formula:

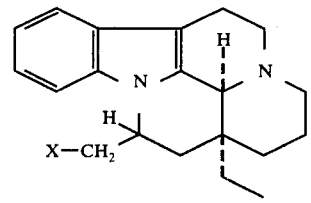

or a pharmaceutically acceptable salt thereof, wherein X is a straight or branched chain lower alkanesulfonyloxy, benzenesulfonyloxy, p-toluenesulfonyloxy, naphthalenesulfonyloxy, thiocyanato, azido, amino, or amino mono- or disubstituted by one of the following groups: $C_1$ to $C_6$ alkyl, $C_2$ to $C_6$ alkenyl, $C_2$ to $C_6$ alkynyl, $C_3$ to $C_{20}$ cycloalkyl, $C_3$ to $C_{20}$ cycloalkenyl, $C_7$ to $C_{20}$ araliphatic, $C_6$ to $C_{14}$ aromatic, acyl group of a carboxylic acid with a $C_1$ to $C_6$ hydrocarbon, acyl group of a carboxylic acid with a $C_1$ to $C_6$ hydrocarbon substituted by halogen, oxo, amino, phenyl, diphenyl or naphthyl, benzoyl, $C_1$ to $C_6$ alkoxycarbonyl, $C_3$ to $C_{20}$ cycloalkyloxycarbonyl, $C_7$ to $C_{20}$ aralkoxycarbonyl, aminocarboimido, and pymolidino, piperidino, perhydroazepino and 4-methylpiperidino group formed with the nitrogen of said amino.

2. A compound as defined in claim 1 of the formula (Ia)

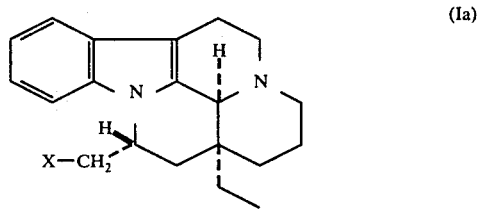

(Ia)

or a pharmaceutically acceptable quaternary salt or acid addition salt thereof.

3. A compound as defined in claim 1 of the formula (Ib)

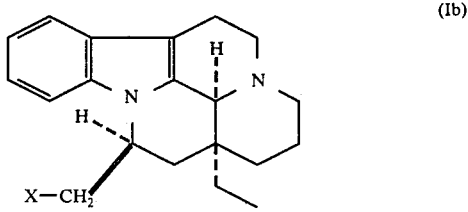

(Ib)

or a pharmaceutically acceptable quaternary salt or acid additional salt thereof.

4. A compound as defined in claim 1 and selected from the group that consists of:

deoxyvincaminol p-toluenesulfonate,
epideoxyvincaminol) p-toluenesulfonate,
14-(thiocyanato-methyl)vincane, 14-(azidomethyl)-vincane, 14-(azidomethyl)-$N_b$-methyl vincanium iodide, 14-(aminomethyl)-vincane dihydrochloride, 14-(dimethylamino-methyl)vincane dihydrochloride, 14-(dimethylamino-methyl)vincane dihydrochloride, 14-(diethylamino-methyl)-vincane dihydrochloride, 14-(pyrrolidino-methyl)-vincane, 14-(pyrrolidino-methyl)-vincane dihydrochloride, 14-(piperidino-methyl)-vincane dihydrochloride, 14-(butylamino-methyl)-vincane, 14-(butylamino-methyl)-vincane dihydrochloride, 14-(allylamino-methyl)-vincane, and 14-(cyclohexylamino-methyl)-vincane p-toluenesulfonate.

5. A compound of the formula:

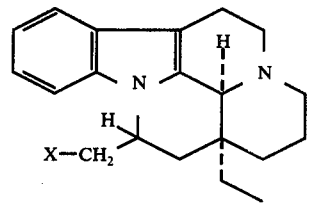

wherein X is selected from the group which consists of:
p-toluene-sulfonyloxy, azido, thiocyanato, amino, dimethylamino, diethylamino, pyrrolidino, piperidino, butylamino, allylamino, cyclohexylamino, benzylamino, acetylamino, ethoxycarbonylamino and guanidino.

6. A compound selected from the group which consists of:
14-(piperidino-methyl)-vincane,
14-(amino-methyl)-vincane,
14-(azidomethyl)-vincane,
14-(acetylamino-methyl)-vincane,
14-(pyrrolidino-methyl)-vincane,
14-(thiocyanato-methyl)-vincane, and
deoxyvincaminol-tosylate.

7. Desoxyvincaminol-tosylate.

* * * * *